United States Patent
Mottola et al.

(10) Patent No.: US 6,179,828 B1
(45) Date of Patent: Jan. 30, 2001

(54) INFUSION SYSTEM WITH FIXED OCCLUDING WIRE

(75) Inventors: Jim Mottola, South Jordan; Stephen W. Carlstrom, Salt Lake City; Stephanie S. Poulsen, Murray; Fred P. Lampropoulos, Sandy, all of UT (US)

(73) Assignee: Merit Medical Systems, Inc., Sandy, UT (US)

(*) Notice: Under 35 U.S.C. 154(b), the term of this patent shall be extended for 0 days.

(21) Appl. No.: 09/273,037

(22) Filed: Mar. 19, 1999

(51) Int. Cl.⁷ .................................................. A61M 25/00
(52) U.S. Cl. ............................ 604/523; 604/256; 604/533
(58) Field of Search ................................. 604/246, 256, 604/523, 533, 528, 264, 164.02, 164.13, 167.01, 284; 600/585; 606/159

(56) References Cited

U.S. PATENT DOCUMENTS

| | | | |
|---|---|---|---|
| 3,585,996 | 6/1971 | Reynolds et al. | 128/214.4 |
| 3,977,400 | 8/1976 | Moorehead | 128/214.4 |
| 4,096,860 | 6/1978 | McLaughlin | 128/214.4 |
| 4,230,123 | 10/1980 | Hawkins, Jr. | 128/658 |
| 4,538,622 | 9/1985 | Samson et al. | 128/772 |
| 4,650,472 | 3/1987 | Bates | 604/158 |
| 4,875,481 * | 10/1989 | Higgins | 128/344 |
| 4,968,307 | 11/1990 | Dake et al. | 604/264 |
| 5,009,391 | 4/1991 | Steigerwald | 251/149.1 |
| 5,062,836 | 11/1991 | Wendell | 604/167 |
| 5,117,839 * | 6/1992 | Dance | 128/772 |
| 5,195,980 | 3/1993 | Catlin | 604/167 |
| 5,250,034 | 10/1993 | Appling et al. | 604/164 |
| 5,267,979 | 12/1993 | Appling et al. | 604/247 |
| 5,334,160 | 8/1994 | Ellis | 604/167 |
| 5,354,275 | 10/1994 | Behnke et al. | 604/86 |
| 5,376,077 | 12/1994 | Gomringer | 604/167 |
| 5,405,323 | 4/1995 | Roger et al. | 604/53 |
| 5,676,671 | 10/1997 | Inoue | 606/108 |
| 5,836,965 | 11/1998 | Jendersee et al. | 606/198 |
| 5,858,002 * | 1/1999 | Jesch | 604/158 |
| 5,951,517 * | 9/1999 | Lampropoulos et al. | 604/151 |

FOREIGN PATENT DOCUMENTS 0 476 796 B1   12/1997   (EP).

OTHER PUBLICATIONS

AngioDynamics®, *Infusion Systems*, Advertisement, Nov. 1998, pp. 1–6.

AngioDynamics®, *Uni*Fuse*, Advertisement, on information and belief, available in the fall of 1998, p. 1.

* cited by examiner

*Primary Examiner*—Glenn K. Dawson
*Assistant Examiner*—Kevin C. Sirmons
(74) *Attorney, Agent, or Firm*—Workman, Nydegger & Seeley (57) ABSTRACT

An improved catheterization system includes (i) an occluding wire; (ii) a catheter, and (iii) a fluid supply port in fluid communication with the catheter. The occluding wire includes (i) an elongate wire body; (ii) an occluding tip coupled to a distal end of the elongate wire body; and (iii) a hub coupled to a proximal end of the elongate wire body. The hub of the occluding wire is configured to be coupled to the catheter. The hub of the occluding wire thus prevents the occluding tip from moving in a longitudinal direction with respect to the catheter once the occluding tip has been placed in a desired position with respect to the catheter.

27 Claims, 5 Drawing Sheets

INFUSION SYSTEM WITH FIXED OCCLUDING WIRE

BACKGROUND OF THE INVENTION

1. The Field of the Invention

This invention is in the field of catheters, including catheterization systems employing occluding wires for use in perfusion catheters.

2. The Relevant Technology

Perfusion catheters have become popular in recent years for use in anesthetizing tissues at an insertion site of a catheter and for treating clotted blood vessels, among other uses. Perfusion catheters typically feature a cannula having infusion holes in a wall thereof for enabling fluid to flow through the wall onto the sensitive tissues of a patient or adjacent an area in which the practitioner has discovered a clot. By positioning the holes of the catheter adjacent the area to be treated, a fluid may be applied to the area, thereby diffusing the clot or anesthetizing the tissues. Once the catheter is positioned at the site of the clot, for example, a thrombolytic fluid capable of dissolving the clot, such as urokinase or streptokinase, is delivered to the site of the clot.

Typical perfusion catheter assemblies comprise a catheter, a fluid supply port, and a hemostasis valve coupled to a proximal end of the catheter which substantially prevents fluid from flowing out a proximal end of the catheter assembly during use. Generally, the distal insertion end of the catheter assembly is open and must therefore be occluded prior to irrigating a liquid from a fluid source through the fluid supply port and into an infusion length of the catheter, where the infusion holes are located. Occlusion of the distal opening of the catheter assembly may be accomplished by inserting an occluding wire through the valve of the assembly and then inserting the wire further along the length of the catheter.

The occluding wire substantially seals the distal end of the infusion catheter during use in order to facilitate spray distribution through the holes. The occluding wire typically includes a wire body portion and a distal sealing ball portion. The sealing ball portion forms a substantially liquid-tight seal at the distal end of the catheter, thereby forcing liquid located proximal to the seal out of the infusion holes of the catheter. Because the inner diameter of the catheter is typically larger than the diameter of the wire body portion of the occluding wire, there is ample space within the infusion catheter for the passage of a liquid out of the infusion holes.

In certain catheters, such as typical 5 French catheters, the inner diameter of the catheter is reduced to a narrow neck at the distal end of the catheter. The sealing ball portion of the occluding wire seats against the inner, narrow neck wall portion of the catheter when inserted into the distal end and thereby substantially occludes the distal opening of the catheter. Consequently, substantially any liquid forced through the catheter is caused to exit through the infusion holes rather than through the opening.

In other catheters, such as typical 4 French catheters, the inner diameter of the catheter is constant throughout the catheter, but the diameter of the occluding ball is configured to substantially match the inner diameter of the catheter. Thus, the practitioner slides the occluding ball to the distal tip, thereby substantially occluding the passageway of the catheter and forcing fluid to flow out of the side perfusion holes proximal to the occluding ball.

When the distal end of the occluding wire is positioned in the catheter, the proximal end of the occluding wire is generally positioned within the hemostasis valve of the catheter assembly. The valve temporarily prevents the occluding wire from moving until the occluding wire is grasped, pushed, or otherwise moved by a practitioner. Consequently, it is generally possible to intentionally or accidentally slide the occluding wire with respect to the catheter, particularly when an adjustable valve is loosened.

Thus, one ramification of present occluding wire and catheter designs is that during use of the catheter system, the proximal end of the occluding wire is generally slidably movable with respect to the hemostasis valve. In addition, the proximal end of the occluding wire generally extends from the proximal end of the catheter assembly and remains exposed to the environment. This dynamic results in a variety of different complications.

For example, the occluding wire can be inadvertently inserted too far distally through the catheter or retracted proximally from a desired position in the catheter. Such inadvertent insertion of the occluding wire may occur when a practitioner accidentally contacts the proximal end of the wire or may be caused by an infusion of fluid under a significant amount of pressure. Such inadvertent actions can cause the occluding wire to lose its occluding effect, for example, by causing the occluding ball to exit the distal opening of the catheter or by inadvertently retracting the ball proximally to a distal set of holes, thereby occluding the fluid supply to the distal set of holes.

In addition to the aforementioned drawbacks associated with typical catheterization systems employing occluding wires, other elongate bodies, such as catheters and guidewires can also be inadvertently displaced from or moved within hemostasis valves.

There is therefore a need in the art for an improved catheterization system for percutaneous catheterization of a blood vessel. More specifically, there is a need in the art for a catheterization system having an improved occluding wire.

SUMMARY AND OBJECTS OF THE INVENTION

It is therefore an object of the invention to provide an improved occluding wire.

It is another object of the invention to provide an improved catheterization system.

It is another object of the invention to provide a catheterization system in which the occluding wire cannot be inadvertently pushed too far into or inadvertently retracted from a catheter.

It is another object of the invention to provide a catheterization system in which the longitudinal position of the occluding wire is fixed with respect to a catheter of the system.

It is another object of the invention to provide a catheterization system in which an elongate body of the system is maintained in a fixed position with respect to a hemostasis valve of the system.

The present invention relates to an improved catheterization system. In one embodiment, the improved catheterization system comprises a perfusion catheterization system comprising: (i) an occluding wire; (ii) a perfusion catheter, and (iii) a fluid supply port in fluid communication with the catheter.

The occluding wire comprises (i) an elongate wire body; (ii) an occluding tip (including an occluding ball or other structure which is larger in diameter than the wire body) coupled to a distal end of the elongate wire body; and (iii)

a hub coupled to a proximal end of the elongate wire body. The hub of the occluding wire prevents the occluding tip from moving in a longitudinal direction with respect to the catheter once the hub has been coupled to the catheter.

The perfusion catheter comprises: (i) a hollow cannula having a cannula wall; and (ii) a hub coupled to the cannula. A lumen extends through the cannula from a proximal opening of the cannula to a distal opening of the cannula. The cannula wall has a plurality of infusion holes extending therethrough. The distal occluding tip of the occluding wire is configured to extend into the lumen of the cannula.

The perfusion catheterization system further comprises a fluid supply port. The fluid supply port supplies fluid to the cannula for delivery through the infusion holes. The fluid supply port can be integral with the catheter or the occluding wire. Optionally, an adaptor comprising a fluid supply port and preferably a hemostasis valve is selectively coupled to the catheter hub so as to be in fluid communication with the cannula.

The adaptor comprises a hollow tubular body having a proximal end and a distal end. The distal end is configured to be coupled to the hub of the catheter. A hollow secondary access tube is coupled at one end thereof in fluid communication with the tubular body of the adaptor. The secondary access tube is configured to be coupled at an opposing end thereof to a fluid source. The secondary access tube thus serves as another example of a fluid supply port for supplying fluid to the cannula. The distal occluding tip of the occluding wire is configured to extend through the hollow tubular body of the adaptor and into the lumen of the cannula. Thus, the occluding wire is positioned within the tubular body of the adaptor and the cannula of the catheter, while fluid is delivered from the secondary access tube, through the tubular body of the adaptor and into the cannula. Upon reaching the distal occluding tip, the fluid is substantially blocked and forced out of the infusion holes proximal to the occluding tip.

The hub of the preferred occluding wire comprises a hub body and a gripping flange extending distally from the hub body. The gripping flange is configured to be coupled to the hub of the catheter, either directly, or by being coupled to the hub of an adaptor, to thereby couple the hub of the occluding wire in a fixed position with respect to the catheter.

The locking hub of the occluding wire of the present invention is particularly useful with straight catheters, i.e., catheters in which the interior surface of the wall of the cannula has substantially the same diameter throughout the length of the cannula. As the occluding tip is positioned within a catheter, the hub of the occluding wire couples to the hub of the catheter, thereby fixing the position of the tip of the occluding wire. This prevents the tip from being extended distally outside of the catheter or moved proximally past the infusion holes of the catheter. Thus, the occluding wire cannot be accidentally pulled from out of the catheter or accidentally pushed through the catheter, thereby insuring a desired fluid flow pattern.

The occluding wire is particularly useful with a 4 French catheter or other catheter which typically does not have a narrowing neck at the distal terminus thereof. In such straight catheters, the occluding tip is freely movable along or out of the catheter in the absence of the locking hub of the present invention.

As another advantage to applicants' system, a substantial variability or tolerance ratio in the distance between the proximal end of the occluding wire and the occluding tip of the wire is allowable. Thus, even if the location of the occluding tip is not exactly positioned as designed with respect to the proximal end of the wire, the occluding wire nevertheless achieves a substantial seal between the occluding tip and the interior surface of the catheter.

In other systems which rely solely on the seating of the ball against a narrowing neck, however, variability or error during the manufacturing process can prevent the mating of the ball against the neck, thereby preventing a desired seal.

In the present invention, a substantial seal is possible both (i) in straight catheters which have no narrowing neck; and (ii) in catheters with a narrowing neck regardless of whether the occluding tip mates with the narrowing neck. Instead of requiring seating against a narrowing neck, the distal end of the occluding wire is selectively located into a desired position when the hub of the occluding wire is located into a desired position. Thus, the catheterization system of the present invention is useful with straight catheters and catheters having a narrowing neck. However, the invented system does not rely solely upon the narrowing neck to form a seal.

Although the locking hub of the present invention is particularly useful with occluding wires used in catheters having infusion holes in the cannula thereof, the locking hub can also be employed in conjunction with a variety of different elongate members used in a variety of different catheters. By locking against a hemostasis valve, for example, the locking hub can assist the valve in blocking fluid flow and can prevent inadvertent movement of the elongate member, such as during the adjustment of an adjustable hemostasis valve.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to improved catheter systems used to treat selected portions of a person's body, such as blood vessels occluded by a thrombus or blood clot. Thrombolytic agents used according to the present invention include any agent that can be used to lyse or break up a blood clot. Examples of preferred thrombolytic fluids include urokinase, streptokinase, and tissue plasminogen activator (TPA), for example.

Figure 1:
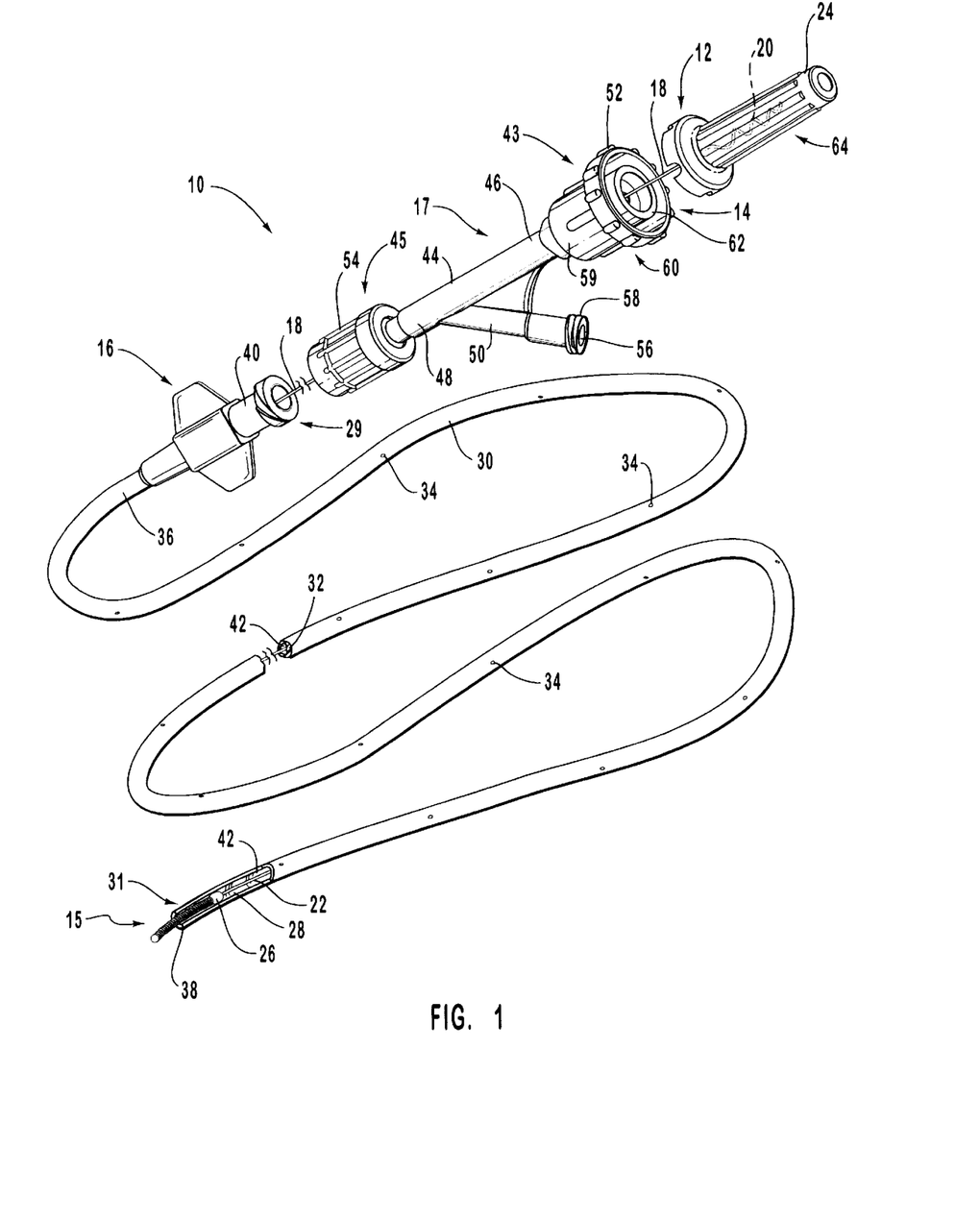
FIG. 1 is a perspective view of a catheterization system of the present invention having an occluding wire positioned within a catheter.

In order to illustrate the benefits of the catheter systems according to the present invention, reference is now made to the drawings. FIG. 1 depicts a catheterization system 10 that may be coupled in fluid communication with a fluid source (not shown). The fluid source may comprise a reservoir, pump, syringe, squeeze bottle, fluid bag, pressurized tank, or other container which can be coupled in fluid communication with system 10, such as through the use of a fluid flow tube, for example.

Catheterization system 10 is configured for percutaneous catheterization of a blood vessel. Catheterization system 10 comprises: (i) an occluding wire 12 (ii) a catheter 16; and (iii) means for coupling catheter 16 in fluid communication with a fluid source.

Occluding wire 12 comprises: (i) an elongate wire body 18 having a proximal end 20 and a distal end 22; (ii) a hub 24 coupled to proximal end 20 of elongate wire body 18; and (iii) an occluding tip 26 coupled to distal end 22 of elongate body 18. Hub 24 and occluding tip 26 may be integrally coupled to wire body 18 or may be coupled thereto through adhesion, welding, or another bonding method.

Catheter 16 has a proximal end 29 and a distal end 31. Catheter 16 comprises a hollow cannula 30 (shown in a partial cross sectional, cutaway view in FIG. 1) having (i) a cannula wall 32; (ii) a proximal end 36 defining a proximal opening; (iii) a distal end 38 defining a distal opening; and (iv) a lumen 28 extending from proximal end 36 to distal end 38. Lumen 28 is sized to receive occluding tip 26 of wire 12. Wall 32 has a plurality of infusion holes 34 extending therethrough.

Catheter 16 further comprises a hub 40 coupled in fluid communication with proximal end 36 of cannula 30. Hub 40 is configured to receive occluding tip 26 of occluding wire 12 therethrough. Hub 40 of catheter 16 may include a male or female lure lock connector or another connector, for example. The catheter presently preferred is a single lumen catheter, although a variety of different catheter embodiments may be employed in the present invention.

Occluding wire 12 of the present invention is particularly useful when employed in conjunction with a catheter having a substantially straight cannula, i.e., a cannula in which the interior surface of the wall of the cannula has substantially the same diameter throughout the length of the cannula, rather than having a cannula which has a neck or other narrowing of the interior surface of the cannula. For example, in FIG. 1, the interior surface 42 of wall 32 of cannula 30 has substantially the same diameter throughout the length of cannula 30. Also by way of example, in one embodiment, the catheter used in the system of the present invention comprises a 4 French catheter.

Occluding wire 12 may be used in conjunction with catheters having internal necks or narrowing portions. However, one major benefit of occluding wire 12 is that such an internal neck is not required to properly seat tip 26 of occluding wire 12 in a desired position within catheter, e.g., distally from infusion holes 34. Instead, tip 26 is maintained in a fixed position with respect to the longitudinal axis of cannula 30 without requiring the narrowing of a neck or tip portion of cannula.

Hub 24 is preferably configured to be selectively coupled to catheter 16. Coupling of an occluding wire hub of the present invention may be direct, i.e. by coupling the occluding wire hub directly to the hub of the catheter. However, in the embodiment of FIG. 1, hub 24 is configured to be selectively coupled to catheter 16 by being selectively coupled to adaptor 17, which is selectively coupled to hub 40 of catheter 16.

Adaptor 17 has a proximal end 43 and a distal end 45. Adaptor 17 comprises a hollow tubular body 44 having a proximal end 46, a distal end 48 and a fluid supply port, such as hollow secondary access tube 50 coupled in fluid communication with tubular body 44 between proximal end 46 and distal end 48. A hub 52 of adaptor 17 is coupled to proximal end 46 of tubular body 44. A rotatable connector 54 is coupled to distal end 48 of tubular body 44.

Connector 54 selectively couples hub 40 of catheter 16 to tubular body 44 of adaptor 17 and hub 52 is configured to be selectively coupled to hub 24 of occluding wire 12. Connector 54 may comprise a male or female lure lock component, for example, for coupling tubular body 44 to hub 40 of catheter 16 such that adaptor 17 is in fluid communication with catheter 16.

Secondary access tube 50 has a central bore 56 formed therethrough so as to be in fluid communication with tubular body 44. A male or female lure lock connector 58 or other connector is disposed on tube 50 in order to couple tube 50 in fluid communication with a fluid source. Secondary access tube 50 can be used to introduce fluids or medical devices into catheter 16.

In one preferred embodiment, adaptor 17 comprises a hemostasis valve assembly 60 and hub 52 comprises a rotating knob 59 of hemostasis valve assembly 60. The hemostasis valve assembly 60 may comprise a slit valve or a touhy borst valve, for example. One primary purpose of the valve assembly 60 is to maintain a fluid seal around elongate wire body 18 or another instrument to prevent the leaking of blood and other bodily fluids as elongate wire body 18 or another instrument is positioned within valve assembly 60.

Hub 52 preferably includes a cylindrically-shaped hollow proximal end portion 62 configured to receive occluding tip 26 therethrough and configured to receive hub 24 of occluding wire 12 thereon. End portion 62 may serve as a proximal end wall of a rotating knob 59 of valve assembly 60, for example. The cylindrically-shaped proximal end portion 62 is merely one example, however, of a structure configured for selectively mating with hub 24 of occluding wire 12.

Once adaptor 17 has been coupled to catheter 16, the process of selectively coupling hub 24 of occluding wire 12 to hub 52 of adaptor 17 immovably fixes the longitudinal position of proximal end 64 of occluding wire 12 and proximal end 43 of adaptor 17 with respect to each other such that distal occluding tip 26 is in a fixed position with respect to cannula 30 of catheter 16. Thus, occluding tip 26 is positioned within catheter 16 so as to substantially occlude the passage of fluid within lumen 28 past occluding tip 26. In the embodiment of FIG. 1, both adaptor 17 and catheter 16 have lumens which are in fluid communication with each other, each lumen being sized to receive the distal end of the occluding wire therethrough.

Adaptor 17 provides valve 60 and a fluid supply port 50 which enables fluid to be delivered into cannula 30. In another embodiment, however, an adaptor having (i) a fluid supply port; or (ii) a valve and a fluid supply port extends integrally from a cannula, catheter hub, or occluding wire hub of the present invention.

Adaptor 17 is an example of adaptor means for defining a first adaptor lumen (within tubular body 44) and a secondary adaptor lumen (within secondary access tube 50) in fluid communication with the first adaptor lumen, wherein (i) distal end 22 of occluding wire 12 is configured to extend through the first adaptor lumen (within tubular body 44) and into lumen 28 of catheter 16; and (ii) the secondary adaptor lumen (within tube 50) is configured to be coupled to a fluid source.

Adaptor 17 is also an example of means for coupling cannula 30 in fluid communication with a fluid source. Other examples of means for coupling a cannula of the present invention in fluid communication with a fluid source include: (i) an adaptor integrally coupled to the cannula, catheter hub, or occluding wire hub; (ii) a tube coupled to the cannula, catheter hub, or occluding wire hub so as to be in fluid communication with the cannula; and (iii) a passageway extending through the cannula, catheter hub, or occluding wire hub so as to be in fluid communication with the cannula. The tube and passageway (and a tube or passageway of an adaptor) are also examples of a fluid supply port in fluid communication with the cannula. The tube may include a male or female Luer lock connector, threads, or another connector for connecting to the fluid source.

The hub of the occluding wire of the present invention may interconnect with the proximal hub of the adaptor or directly to the hub of the catheter in a variety of different manners, such as through the use of Luer lock components, mating threads, or a variety of different couplings. Preferably, however, hub 24 is press-fit onto hub 52 of adaptor 17.

Figure 2:
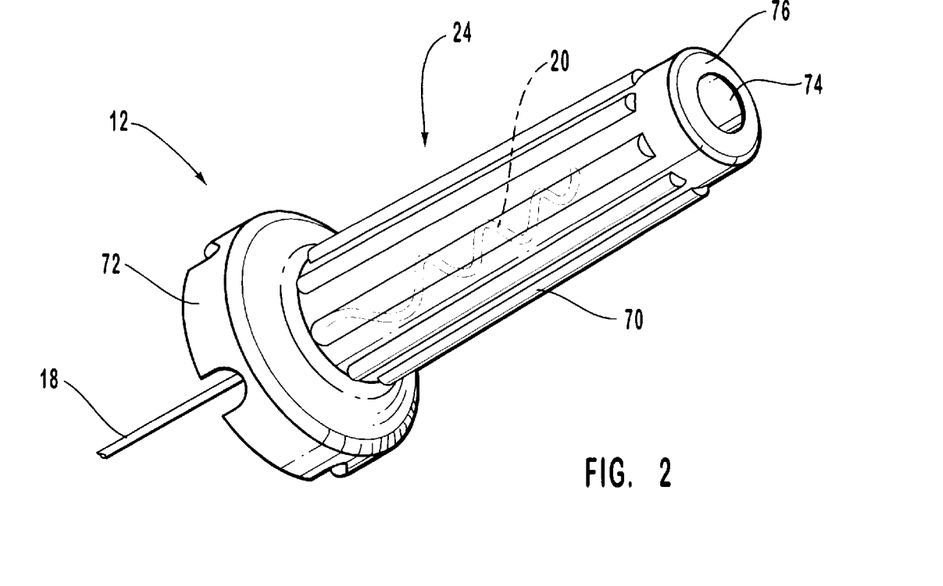
FIG. 2 is a perspective view of the hub of the occluding wire of FIG. 1 shown from a rear view.

With reference now to FIG. 2, hub 24 of occluding wire 12 comprises: (i) a hollow hub body 70 coupled to proximal end 20 of elongate wire body 18; and (ii) a substantially circular gripping flange 72 extending distally from hub body 70. Flange 72 of FIG. 2 is configured to be selectively mounted on hollow cylindrical end portion 62 of adaptor 17.

As shown in a phantom view in FIG. 2, proximal end 20 of elongate wire body is received within a chamber 74 of hub body 70. Proximal end 20 of elongate wire body 18 is preferably immovably coupled to hub body 70 by an adhesive disposed within chamber 74 of hub body 70.

Figure 3:
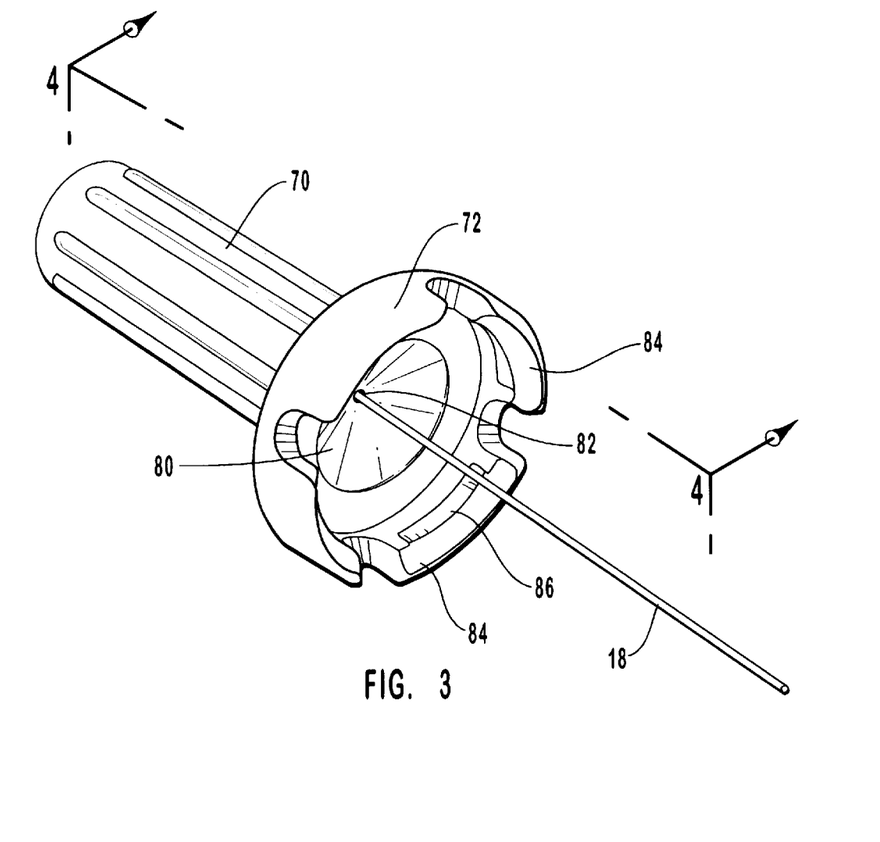
FIG. 3 is a perspective view of the hub of FIG. 2 shown from a frontal view.

With reference now to FIGS. 2 and 3, chamber 74 of hub body 70 extends from a proximal end 76 of hub body 70 to a distal conically shaped face 80 of hub body 70. At distal face 80, hollow body 70 narrows to a small opening 82 configured to mount a portion of wire body 18 therein.

Gripping flange 72 comprises a plurality of snap tabs 84 extending distally from face 80 of hub body 70. Snap tabs 84 are oriented in a substantially circular configuration to thereby selectively grip a cylindrical end portion 62 of hub 52 of adaptor 17 therebetween. In one embodiment, snap tabs 84 move resiliently outwardly when the practitioner couples hub 24 of wire 12 to hub 52 of adaptor 17. To increase the gripping action of tabs 84, internal ridges 86 are positioned on respective snap tabs 84. Optionally, a circular ridge is disposed about cylindrical end portion 62 of hub 52 and ridges 86 selectively snap over the circular ridge.

Figure 4:
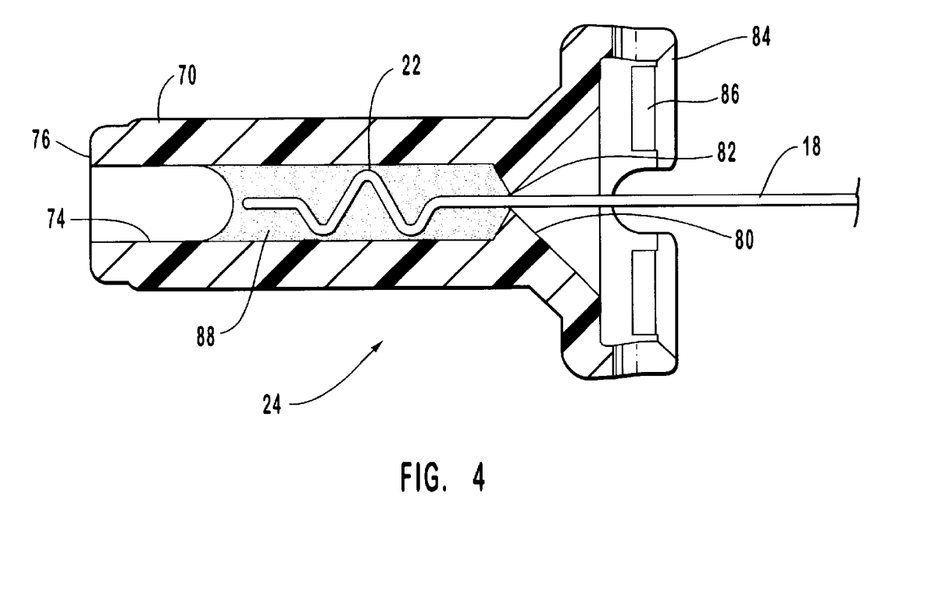
FIG. 4 is a cross sectional view of the hub of FIGS. 2 and 3.

With reference now to FIG. 4, proximal end 22 of wire body 12 is preferably secured within hub 24 through the use of an adhesive material 88 disposed within chamber 74. Adhesive 88 is preferably a light curable adhesive and hub body 70 is preferably light permeable such that adhesive 88 can be activated through emission of light radiation through body 70. Preferably, proximal end 22 is also crimped, as shown.

One preferred method for coupling hub 24 to wire body 18 comprises placing an uncrimped proximal end of wire body 18 through opening 82 in conical face 80 of hub 24 until the proximal end exits proximal end 76 of chamber 74. The proximal end is then crimped and retracted back into chamber 74. Adhesive 88 is then placed in chamber 74 and cured, immovably coupling proximal end 22 to hub 24. Other methods for immovably coupling the proximal end of the wire body and the hub include forming the hub integrally with the wire body, ultrasonic bonding, epoxy bonding, insert molding, welding, or a variety of different coupling techniques.

Hub 24 is an example of means for selectively fixing the longitudinal position of distal end 22 of occluding wire 12 in a fixed position with respect to catheter 16 such that distal end 22 of occluding wire 12 is positioned with respect to catheter 16 so as to substantially occlude the passage of fluid within cannula 30 past tip 26.

Figure 5:
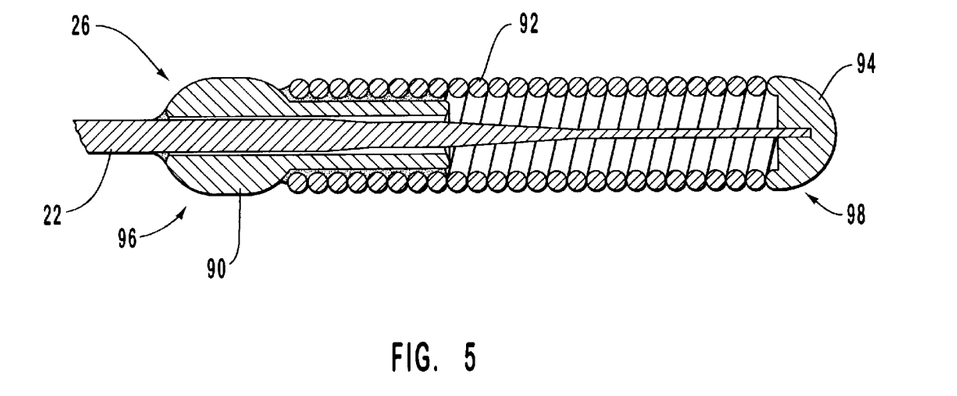
FIG. 5 is a cross sectional view of the occluding tip of the occluding wire of FIG. 1.

With reference now to FIG. 5, occluding tip 26 has an occluding ball 90 coupled to distal end 22 of wire body 18. A spring coil 92 having a distal rounded tip 94 is coupled to occluding ball 90. Occluding tip 26 is an example of occluding means coupled to distal end 22 of elongate wire body 18 for substantially occluding the lumen 28 of catheter 16. However, a variety of different tips may be employed in the present invention for substantially occluding the lumen 28 of catheter 16, including tips having various shapes and configurations and which are larger in diameter than wire body 18.

Tip 26 is configured to have a diameter which will allow sliding of tip 26 through cannula 30, yet enable tip 26 to substantially occlude cannula 30. Thus, the practitioner slides tip 26 to a desired position within cannula 30, e.g., past occluding holes 34, to thereby substantially occlude the passageway of cannula 30 and force fluid to flow out of holes 34.

Hub 24 maintains at least a portion of tip 26 within cannula 30 during use. In one embodiment, the entire tip 26 is positioned within cannula 30 during delivery of fluid. However, in another embodiment, portions of tip 26, such as rounded tip 94, tip 94 and coil 92, or tip 94 and a portion of coil 92 may extend from the distal end of cannula 30 while ball 90 remains therein during delivery of fluid.

As shown in FIG. 5, tip 26 has a substantially uniform diameter from ball 90 through spring coil 92 and to tip 94. Thus, tip 26 has a substantially uniform diameter from a proximal end 96 to a distal end 98 thereof. In one embodiment, for example, the diameter of ball 90 is slightly larger than that of coil 92 and rounded tip 94, but the diameter of tip 26 is nevertheless substantially uniform from proximal end 96 to distal end 98. This substantially uniform diameter provides for convenient and smooth sliding of tip 94 through cannula 30, as opposed to systems having a ball which is dramatically larger than the spring coil. Ball 90 may be have an oblong configuration, as shown in FIG. 5, to contribute to the substantial uniformity of tip 26.

Catheter 16 and adaptor 17 of FIG. 1 collectively serve as an example of catheter means for defining a fluid flow path, the catheter means having a proximal end 14 and a distal end 15. The fluid flow path of the catheter means shown in FIG. 1 includes the lumen 28 of cannula 30 and the first adaptor lumen defined by tubular body 44 of adaptor 17. As will be appreciated from the discussion above, however, the catheter means may comprise a variety of different structures which can accomplish the goals and designs of the present invention.

Figure 6:
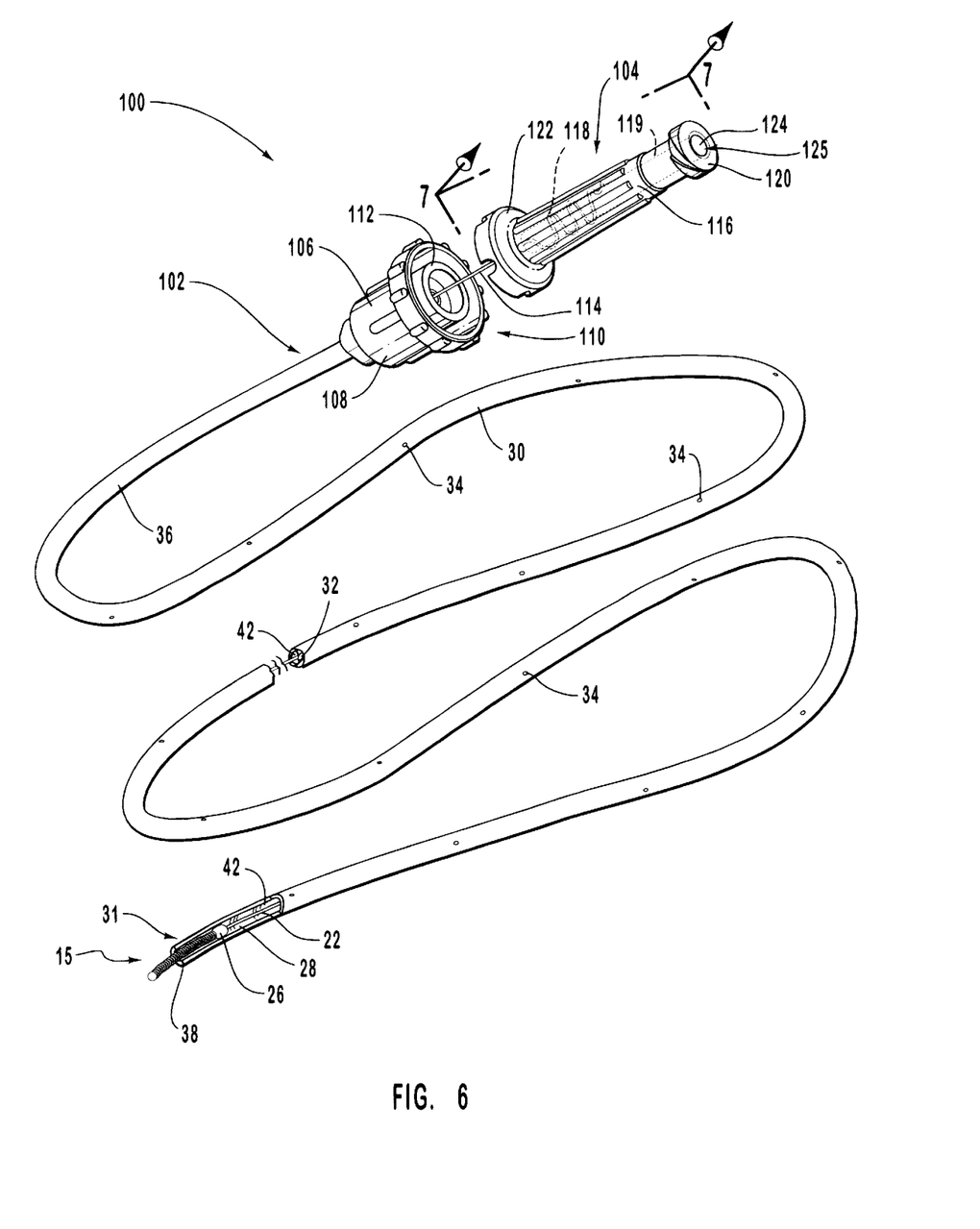
FIG. 6 is a perspective view of another catheterization system of the present invention.

FIG. 6 demonstrates another example of a catheterization system 100 of the present invention. Catheterization system 100 comprises a catheter 102 and an occluding wire 104. Catheter 102 is another example of catheter means for defining a fluid flow path. Catheter 102 comprises: (i) a cannula 30 as discussed above with reference to FIG. 1; and (ii) a hub 106 coupled in fluid communication with cannula 30. Hub 106 comprises a rotating knob 108 of a hemostasis valve assembly 110. Hub 106 includes hollow proximal end portion 112 configured to receive occluding tip 26 therethrough.

Occluding wire 104 comprises an elongate wire body 114 and a hub 116 coupled to proximal end 118 of elongate wire body 114. Hub 116 comprises a hollow hub body 119, a connector 120, such as a male or female Luer lock connector, coupled to one end of hub body 119, and a gripping flange 122 extending from an opposing end of hollow hub body 119. Hub body 119 has an interior surface 124 defining a fluid flow passageway 125 therethrough.

Gripping flange 122 is configured to be selectively mounted onto proximal end portion 112 of hub 106 and connector 120 is configured to be selectively coupled to a fluid source. Passageway 125 defined by hollow interior surface 124, serves as an example of means for coupling cannula 30 in fluid communication with a fluid source. Connector 120 in fluid communication with passageway 125 also serves as an example of means for coupling cannula 30 in fluid communication with a fluid source. Thus, a fluid source may be coupled directly to a passageway within a hub or cannula, such as by being inserted therein, but is preferably selectively coupled to a connector in fluid communication with the passageway.

Figure 7:
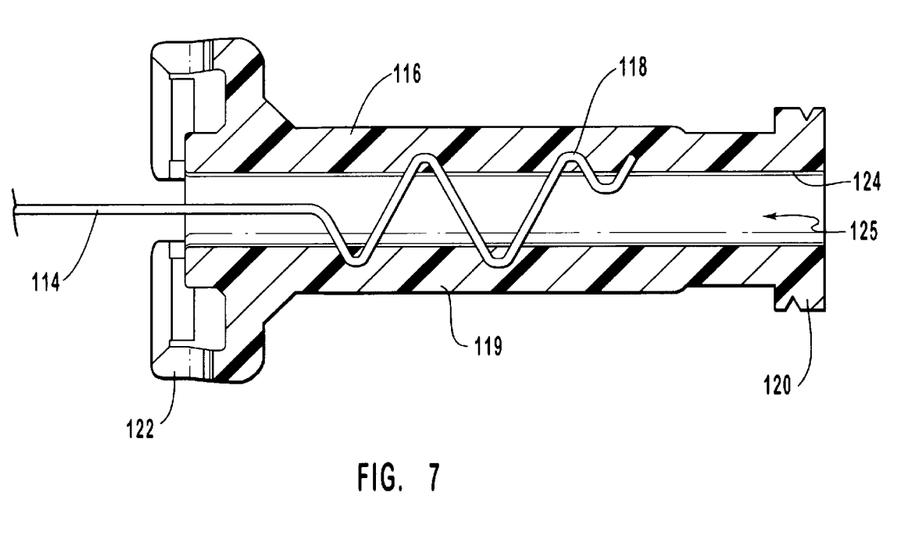
FIG. 7 is a cross sectional view of the hub of FIG. 6.

Hub 116 coupled to proximal end 118 is shown in additional detail in FIG. 7. As shown, in one embodiment, proximal end 118 is coupled within interior surface 124 of hub 116 by being imbedded into hub 116 or by having hub 116 molded about proximal end 118.

The catheter means of the present invention may comprise a hemostasis valve as discussed above. However, in another embodiment, the hub of the occluding wire serves to stop the flow of blood between the catheter or adaptor and the environment.

Although hub 24 and hub 116 are shown in FIGS. 1–7 as being coupled to respective elongate wire bodies, occluding wires 12 and 104 are each examples of elongate instruments having an elongate body and means for selectively fixing the longitudinal position of the distal end of the elongate body in a fixed position with respect to the catheter means. Additional examples of elongate bodies which can be coupled to hub 24 or hub 116 or another such hub of the present invention include guidewires, catheters, various cannulas, and a variety of other elongate bodies known in the art and yet to be produced.

A hub, such as hub 24 or 116 can readily couple such elongate bodies to a corresponding hub on a hemostasis valve or other structure which is coupled to a catheter (which may comprise a cannula with or without infusion holes, for example). In addition to selectively locating the distal end of the elongate body in a fixed position with respect to the catheter, such coupling assists in preventing the flow of liquid from the valve. Furthermore, such coupling adds convenience to the use of adjustable valves since the locking hub can assist the valve in blocking fluid flow while the practitioner is still able to manipulate a rotating knob of the valve to adjust the hemostasis valve, for example.

Examples of hemostasis valves which may be employed in the present invention are disclosed in U.S. Pat. No. 5,591,137 entitled "Hemostasis Valve with Locking Seal, U.S. Pat. No. 5,651,170 entitled "Method For Positioning A Split Ring Over an Enlarged Flange, U.S. Pat. No. 5,693,025 entitled Adapter with Hemostasis Valve and Rotatable Connector, U.S. patent application Ser. No. 08/950,627, filed Oct. 15, 1997 entitled "Improved Hemostasis Valve with Catheter/Guidewire Seals," and U.S. patent application Ser. No. 08/978,492 filed on Nov. 25, 1997, entitled "Valve Apparatus with Adjustable Quick-Release Mechanism," each of which are incorporated herein by reference.

The cannula 30 of the present invention preferably comprises a flexible material, such as flexible nylon, while the catheter hub 40 comprises a more rigid nylon or other material. Adaptor 17 and wire hub 24 preferably comprises a substantially rigid material, such as polycarbonate. Wire body 18 and tip 26 are preferably comprised of a thin metallic material, such as stainless steel.

In yet another aspect of the present invention, a cap is configured to be selectively coupled to a proximal end of a hemostasis valve. The cap may be configured similar to hub 24, but without an opening 82 in distal face 80, for example, and without an elongate wire body coupled thereto. The cap can be snap fitted onto proximal end 62 of hub 52 for example, and may be used as a cover to maintain the proximal opening of the hemostasis valve in a sterile condition, for example, and to assist in the prevention of blood flow.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheterization system for percutaneous catheterization of a blood vessel, comprising:
   catheter means for defining a fluid flow path, the catheter means having a proximal end and a distal end, the catheter means comprising: a hollow cannula having (i) a cannula wall having a plurality of infusion holes extending therethrough; (ii) a proximal end defining a proximal opening; (iii) a distal end defining a distal opening; and (iv) a lumen extending from the proximal end of the cannula to the distal end of the cannula; and
   an occluding wire having a proximal end and a distal end, the occluding wire comprising:
   (i) an elongate wire body having a proximal end and a distal end;
   (ii) occluding means coupled to the distal end of the elongate wire body for substantially occluding the lumen of the cannula; and
   (iii) means for externally coupling the occluding wire to the proximal end of the catheter means, so as to selectively fix the longitudinal position of the distal end of the occluding wire in an immovably fixed position with respect to the catheter means such that the distal end of the occluding wire is positioned with respect to the catheter means so as to substantially occlude the passage of fluid within the cannula past the occluding means of the occluding wire.

2. A catheterization system as recited in claim 1, wherein the means for selectively fixing the longitudinal position of the distal end of the occluding wire comprises a hub coupled to the proximal end of the elongate wire body of the occluding wire.

3. A catheterization system as recited in claim 2, wherein the hub of the occluding wire is configured to be selectively coupled to the proximal end of the catheter means.

4. A catheterization system as recited in claim 2, wherein the hub of the occluding wire comprises:
  i. a hub body coupled to the proximal end of the elongate wire body; and
  ii. a gripping flange extending distally from the hub body.

5. A catheterization system as recited in claim 2, wherein the catheter means comprises a hub coupled to the proximal end of the cannula which is configured to receive the occluding tip of the occluding wire therethrough and is configured to be coupled to the hub of the occluding wire.

6. A catheterization system as recited in claim 5, wherein the catheter means comprises an adaptor configured to be coupled between the hub coupled to the proximal end of the cannula and the hub of the occluding wire.

7. A catheterization system as recited in claim 6, wherein the adaptor is configured to be selectively coupled to the hub coupled to the proximal end of the cannula.

8. A catheterization system as recited in claim 1, wherein the catheterization system comprises means for coupling the cannula in fluid communication with a fluid source.

9. A catheterization system as recited in claim 8, wherein the means for coupling the cannula in fluid communication with a fluid source comprises a fluid supply port in fluid communication with the cannula.

10. A catheterization system as recited in claim 8, wherein the means for coupling the cannula in fluid communication with a fluid source comprises adaptor means for defining (i) a first adaptor lumen; and (ii) a secondary adaptor lumen in fluid communication with the first adaptor lumen, wherein (i) the distal end of the occluding wire is configured to extend through the first adaptor lumen and into the lumen of the cannula; and (ii) the secondary adaptor lumen is configured to be coupled to a fluid source.

11. A catheterization system as recited in claim 8, wherein the means for coupling the cannula in fluid communication with a fluid source comprises a passageway extending through the means for selectively fixing the longitudinal position of the distal end of the occluding wire in a fixed position.

12. A catheterization system as recited in claim 1, wherein the interior surface of the wall of the cannula has substantially the same diameter throughout the length of the cannula.

13. A catheterization system for percutaneous catheterization of a blood vessel, comprising:
  a catheter comprising a hollow cannula having (i) a cannula wall having a plurality of infusion holes extending therethrough; (ii) a proximal end defining a proximal opening; (iii) a distal end defining a distal opening; and (iv) a lumen extending from the proximal end of the cannula to the distal end of the cannula; and
  an occluding wire having a proximal end and a distal end, the occluding wire comprising:
    (i) an elongate wire body having a proximal end and a distal end;
    (ii) an occluding tip coupled to the distal end of the elongate wire body; and
    (iii) a hub coupled to the proximal end of the elongate wire body of the occluding wire, the hub being irremovably connected to the occluding wire at a distance from the distal tip thereof that is selected so that when the hub is coupled to the catheter the occluding tip is in position with respect to occluding the distal tip of the catheter.

14. A catheterization system as recited in claim 13, wherein the hub of the occluding wire comprises:
  i. a hub body; and
  ii. a gripping flange extending distally from the hub body.

15. A catheterization system as recited in claim 13, wherein the hub of the occluding wire comprises a hub body and a proximal end of the elongate wire body is received within a chamber of the hub body.

16. A catheterization system as recited in claim 15, wherein the proximal end of the elongate wire body is immovably coupled to the hub body through the use of an adhesive disposed within the chamber of the hub body.

17. A catheterization system as recited in claim 13, wherein the interior surface of the wall of the cannula has substantially the same diameter throughout the length of the cannula.

18. A catheterization system as recited in claim 13, further comprising means for coupling the catheter in fluid communication with a fluid source.

19. A catheterization system as recited in claim 18, wherein the means for coupling the catheter in fluid communication with a fluid source comprises an adaptor comprising:
  (i) a hollow tubular body having a proximal end and a distal end, the distal end configured to be coupled to the proximal end of the catheter and the proximal end configured to be coupled to the hub of the occluding wire; and
  (ii) a fluid supply port in fluid communication with the tubular body; wherein the distal end of the occluding wire is configured to extend through the hollow tubular body and into the lumen of the cannula and the fluid supply port is configured to be coupled to a fluid source.

20. A catheterization system as recited in claim 19, wherein the adaptor is configured to be selectively coupled between the proximal end of the catheter and the hub of the occluding wire.

21. A catheterization system as recited in claim 18, wherein the means for coupling the cannula in fluid communication with a fluid source comprises the hub having a passageway extending therethrough, the passageway being in fluid communication with the cannula.

22. A catheterization system as recited in claim 21, wherein the hub comprises a hub body and a Luer lock connector coupled to a proximal end of the hub body.

23. A catheterization system as recited in claim 13, wherein the occluding tip has a substantially uniform diameter from a proximal end to a distal end thereof.

24. A catheterization system for percutaneous catheterization of a blood vessel, comprising:
  a catheter comprising a hollow cannula having (i) a cannula wall having a plurality of infusion holes extending therethrough; (ii) a proximal end defining a proximal opening; (iii) a distal end defining a distal opening; and (iv) a lumen extending from the proximal end of the cannula to the distal end of the cannula; and
  (v) a hub coupled to the proximal end of the cannula;
  an occluding wire having a proximal end and a distal end, the occluding wire comprising:
    (i) an elongate wire body having a proximal end and a distal end;
    (ii) an occluding tip coupled to the distal end of the elongate wire body; and
    (iii) a hub irremovably coupled to the proximal end of the elongate wire body of the occluding wire at a distance from the distal end thereof so that when the hub of the occluding wire is coupled to the catheter by way of an adapter the occluding tip is in position with respect to the occluding the distal opening of the catheter; and an adaptor comprising:
  (i) a hollow tubular body having a proximal end and a distal end, the distal end configured to be coupled to the hub of the catheter and the proximal end configured to be coupled to the hub of the occluding wire; and
  (ii) a fluid supply port in fluid communication with the tubular body; wherein the distal end of the occluding wire is configured to extend through the hollow tubular body and into the lumen of the cannula and wherein the fluid supply port is configured to be coupled to a fluid source, the hub of the occluding wire configured to be coupled to the adaptor such that the occluding tip is in a fixed position with respect to the catheter.

25. A catheterization system as recited in claim 24, wherein the adaptor is configured to be selectively coupled to the hub of the catheter.

26. A catheterization system for percutaneous catheterization of a blood vessel, comprising:

catheter means for defining a fluid flow path, the catheter means having a proximal end and a distal end, the catheter means comprising:

(A) a hollow cannula having (i) a cannula wall; (ii) a proximal end defining a proximal opening; (iii) a distal end defining a distal opening; and (iv) a lumen extending from the proximal end of the cannula to the distal end of the cannula; and
  (B) a hemostasis valve coupled in fluid communication with the hollow cannula, the hemostasis valve having a proximal end and a distal end; and an elongate instrument having a proximal end and a distal end, the elongate instrument comprising:
    (i) an elongate body having a proximal end and a distal end; and
    (iii) means for externally coupling an occluding wire to the proximal end of the catheter means, so as to selectively fix the longitudinal position of the distal end of the occluding wire in an immovably fixed position with respect to the catheter means such that the distal end of the occluding wire is positioned with respect to the catheter means so as to substantially occlude the passage of fluid within the cannula past the occluding means of the occluding wire.

27. A catheterization system as recited in claim 26, wherein the means for selectively fixing comprises a hub coupled to the proximal end of the elongate body.

* * * * *

UNITED STATES PATENT AND TRADEMARK OFFICE
CERTIFICATE OF CORRECTION

PATENT NO. : 6,179,828 B1
DATED : January 30, 2001
INVENTOR(S) : Jim Mottola, Stephen W. Carlstrom, Stephanie S. Poulsen and Fred P. Lampropoulos It is certified that error appears in the above-identified patent and that said Letters Patent is hereby corrected as shown below:

Column 5,
Line 41, after "female" change "lure" to -- luer --

Column 6,
Line 18, after "female" change "lure" to -- luer --
Line 24, after "female" change "lure" to -- luer --

Column 8,
Line 54, before "have an" delete "be"

Signed and Sealed this

Twenty-eighth Day of May, 2002

Attest:

Attesting Officer

JAMES E. ROGAN
*Director of the United States Patent and Trademark Office*